United States Patent
Johansson et al.

(10) Patent No.: US 9,238,058 B2
(45) Date of Patent: *Jan. 19, 2016

(54) RECONSTITUTED SURFACTANTS HAVING IMPROVED PROPERTIES

(75) Inventors: Jan Johansson, Parma (IT); Tore Curstedt, Parma (IT); Bengt Robertson, Parma (IT); Joakim Robertson, Solna (SE); Soeren Robertson, Stockholm (SE); Magnus Robertson, Sollentuna (SE); Charlotte Robertson, Goeteborg (SE); Gertie Robertson Grossmann, Stockholm (SE)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,164

(22) Filed: Apr. 10, 2012
(Under 37 CFR 1.47)

(65) Prior Publication Data
US 2013/0079275 A1    Mar. 28, 2013

Related U.S. Application Data

(63) Continuation of application No. 12/422,581, filed on Apr. 13, 2009, now Pat. No. 8,183,210, which is a continuation of application No. PCT/IB2007/002841, filed on Sep. 28, 2007.

(30) Foreign Application Priority Data

Oct. 13, 2006   (EP) ..................................... 06021521

(51) Int. Cl.
*A61K 38/00* (2006.01)
*A61K 38/17* (2006.01)
*C07K 14/785* (2006.01)

(52) U.S. Cl.
CPC ............. *A61K 38/395* (2013.01); *C07K 14/785* (2013.01); *A61K 38/00* (2013.01)

(58) Field of Classification Search
None
See application file for complete search history.

(56) References Cited

U.S. PATENT DOCUMENTS

| 5,653,996 | A  | * | 8/1997  | Hsu .............................. 424/450 |
| 7,053,044 | B1 | * | 5/2006  | Curstedt et al. .............. 514/18.2 |
| 2008/0242589 | A1 | | 10/2008 | Curstedt et al. |
| 2009/0075892 | A1 | | 3/2009  | Johansson et al. |
| 2009/0088379 | A1 | | 4/2009  | Johansson et al. |

FOREIGN PATENT DOCUMENTS

| EP | 1 481 665 | | 12/2004 |
| WO | 00/47623 | | 8/2000 |
| WO | WO 00/47623 | * | 8/2000 |
| WO | WO 2008/011559 | * | 1/2008 |

OTHER PUBLICATIONS

Waring A J et al., "The role of charged amphipathic helices in the structure and function of surfactant protein B", Journal of Peptide Research, vol. 66, No. 6, Dec. 2005, pp. 364-374.
Palmblad et al., "Biophysical activity of an artificial surfactant containing an analogue of surfactant protein (SP)-C and native SP-B", Biochemical Journal, Portland Press, London, GB, vol. 339, No. 2, 1999, pp. 381-386.
Walther Frans J et al., "Hydrophobic surfactant proteins and their analogues", Neonatology, Karger, Basel, Ch, vol. 91, No. 4, 2007, pp. 303-310.
Walther F J et al., "Surfactant Protein B and C Analogues", Molecular Genetics and Metabolism, Academic Press, San Diego, CA, US, vol. 71, No. 1/2, 2000, pp. 342-351..
Curstedt et al., Biol. Neonate, vol. 87, pp. 332-337 (2005).
U.S. Appl. No. 14/085,125, filed Nov. 20, 2013, Johansson, et al.

* cited by examiner

*Primary Examiner* — Karlheinz R Skowronek
*Assistant Examiner* — Roy Teller
(74) *Attorney, Agent, or Firm* — Oblon, McClelland, Maier & Neustadt, L.L.P.

(57) ABSTRACT

Reconstituted surfactants comprising a lipid carrier, a polypeptide analog of the native surfactant protein SP-C, and a polypeptide analog of the native surfactant protein SP-B are useful for the treatment and/or prophylaxis of RDS and other respiratory disorders.

20 Claims, 2 Drawing Sheets

Fig. 1

| NH2 | Phe 1 | Gly | Ile | Pro | Cys 5 | Cys | Pro | Val | His | Leu 10 | Lys |
| --- | --- | --- | --- | --- | --- | --- | --- | --- | --- | --- | --- |
| | | Arg | Leu | Leu | Iso 15 | Val | Val | Val | Val | Val 20 | Val |
| | | Leu | Ile | Val | Val 25 | Val | Ile | Val | Gly | Ala 30 | Leu |
| | | Leu | Met | Gly | Leu | COOH | | | | | |

Fig. 2

Phe Pro Ile Pro Leu Pro Tyr Cys Trp Leu Cys Arg Ala Leu Ile Lys
1           5               10              15

Arg Ile Gln Ala Met Ile Pro Lys Gly Ala Leu Ala Val Ala Val Ala
        20              25              30

Gln Val Cys Arg Val Val Pro Leu Val Ala Gly Gly Ile Cys Gln Cys
        35              40              45

Leu Ala Glu Arg Tyr Ser Val Ile Leu Asp Thr Leu Leu Gly Arg
        50              55              60

Met Leu Pro Gln Leu Val Cys Arg Leu Val Leu Arg Cys Ser Met
65              70              75

RECONSTITUTED SURFACTANTS HAVING IMPROVED PROPERTIES

CROSS REFERENCES TO RELATED APPLICATIONS

This application is a continuation of U.S. patent application Ser. No. 12/422,581, filed on Apr. 13, 2009, now U.S. Pat. No. 8,183,210, which was a continuation of International Patent Application No. PCT/IB2007/002841, filed on Sep. 28, 2007, and claims priority to European Patent Application No. 06021521.7, filed on Oct. 13, 2006, both of which are incorporated herein by reference in their entireties.

BACKGROUND OF THE INVENTION

1. Field of the Invention

The present invention relates to reconstituted surfactants which are useful for the treatment or prophylaxis of RDS and other respiratory disorders. The present invention also relates to methods of preparing such a reconstituted surfactant and pharmaceutical compositions which contain such a reconstituted surfactant. The present invention further relates to methods for the treatment or prophylaxis of RDS and other respiratory disorders by administering such a reconstituted surfactant.

2. Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is composed primarily of lipid and contains minor amounts of various proteins. An absence of adequate levels of this complex results in malfunction of the lung. This syndrome is called Respiratory Distress Syndrome (RDS) and it commonly affects preterm infants.

Said syndrome is effectively treated with modified natural surfactant preparations extracted from animal lungs. Commercially available modified surfactant preparations are, for example, Curosurf, derived from porcine lung, Infasurf, extracted form calf lung lavage, and Survanta, a chemically modified natural bovine lung extract.

The main constituents of these surfactant preparations are phospholipids, such as 1,2-dipalmitoyl-sn-glycero-3-phosphocholine commonly known as dipalmitoylphosphatidylcholine (DPPC), phosphatidylglycerol (PG), and surfactant hydrophobic proteins B and C (SP-B and SP-C).

Due to the drawbacks of the surfactant preparations from animal tissues, such as the complication of the production and sterilization processes and possible induction of immune reactions, synthetic surfactants mimicking the composition of the modified natural surfactants have been developed. Said synthetic surfactants are known as reconstituted surfactants. However the development of clinically active reconstituted surfactants has turned out to be complicated since the native hydrophobic proteins are too big to synthesize, structurally complex, and unstable in pure form.

In order to replace said native hydrophobic proteins, some synthetic polypeptides partially corresponding to their sequences and analogs thereof have been proposed in the prior art and are disclosed in for example WO 89/06657, WO 92/22315, WO 98/49191, WO 95/32992, U.S. Pat. No. 6,660,833, EP 413,957, and WO 91/18015.

WO 00/47623 disclosed synthetic polypeptides which are analogs of the native protein SP-C wherein: i) cysteine residues in position 5 and 6 have been replaced by Ser residues; ii) the Val residues of the 'center region' of SP-C have been substituted with other neutral and hydrophobic residues selected from the group consisting of Leu, Ile, and norleucine (nL); iii) some of the neutral amino acids present in the 'center region' of SP-C have been replaced with bulky or polar residues selected from the group consisting of Lys, Trp, Phe, Tyr, and Ornithine. Said artificial polypeptides are characterized by the fact that they are capable of folding like the native protein SP-C and, hence, interacting properly with the surfactant lipids and, thus, do not give rise to self-oligomerization.

WO 00/76535 generically discloses pulmonary surfactant preparations comprising at least one modification of the SP-B in combination with at least one modification of the SP-C protein.

In A. J. Waring, et al., (abstract presented at the Paediatric Academy Society Annual meeting held in San Francisco on Apr. 29-May 2, 2006) a study was undertaken to examine the activity of a synthetic surfactant constituted of the SP-C-mimic, SP-Cff, that is a synthetic 34-residue SP-C with phenylalanine instead of cysteine in positions 4 and 5, and the SP-B-mimic, Mini-B.

However, according to the available literature, in animal studies, the treatment with reconstituted surfactants gives rise to poor lung gas volumes and grade of alveolar patency at the end of expiration, and a ventilation is required with a positive end expiratory pressure (PEEP) in order to achieve an in vivo activity comparable to that achieved with modified natural surfactants (see, J. Johansson, et al., *J. Appl. Physiol.*, 2003, 95, 2055-2063; and A. J. Davis, et al., *Am. J. Respir. Crit. Care Med.*, 1998; 157, 553-559). Thus, the available reconstituted surfactant preparations are indeed not capable of forming a stable phospholipidic film in the alveoli at the end of expiration.

Moreover, all of the aforementioned documents are silent about the problem of the alveolar patency at the end of expiration and the effect of the disclosed preparations thereof.

Thus, there remains a need for a reconstituted surfactant with improved properties in terms of lung compliance.

SUMMARY OF THE INVENTION

Accordingly, it is one object of the present invention to provide novel reconstituted surfactants which are useful for the treatment or prophylaxis of RDS and other respiratory disorders.

It is another object of the present invention to provide novel reconstituted surfactants which are capable of guaranteeing alveolar stability, and hence maintaining alveolar patency at the end of expiration without requiring ventilation with PEEP.

It is another object of the present invention to provide novel methods of preparing such a reconstituted surfactant.

It is another object of the present invention to provide novel pharmaceutical compositions which contain such a reconstituted surfactant.

It is another object of the present invention to provide novel methods of treating and/or preventing RDS and other respiratory disorders by administering such a reconstituted surfactant.

These and other objects, which will become apparent during the following detailed description, have been achieved by the inventors' discovery that particular analogues of the native SP-C protein, and preferably the polypeptides of WO 00/47623 can advantageously be combined with particular analogues of the native protein SP-B in order to provide a reconstituted surfactant preparation with improved properties in terms of lung compliance, and in particular the ability to efficaciously maintain alveolar patency at the end of expiration without requiring ventilation with PEEP.

Thus, in a first embodiment, the present invention provides a reconstituted surfactant comprising a lipid carrier, and a combination of a particular polypeptide analog of the native surfactant protein SP-C with a particular polypeptide analog of the native surfactant protein SP-B.

In particular the invention provides a reconstituted surfactant comprising:
a) a lipid carrier;
b) a polypeptide of at least 20 amino acid residues and no more than 40 amino acid residues having the sequence represented by the general formula (I) (SEQ ID NO: 10):

$$F_e G_e I_f P_f S_g \text{SPVHLKRX}_a \text{BX}_b (\text{BX}_c)_n \text{GALL}_n \Omega_p G_p L_p \qquad (I)$$

wherein:
each X is independently an amino acid residue selected from the group consisting of I, L, and nL;
each B is independently an amino acid residue selected from the group consisting of K, R, H, W, F, Y, and Orn;
each S is independently optionally substituted with an acyl group containing 12-22 carbon atoms, preferably 16 carbon atoms, linked to the side chain via an ester bond;
$\Omega$ is an amino acid selected from the group consisting of M or M oxidized on the sulfur atom, I, L, and nL;
a is an integer having a value of 1 to 8;
b is an integer having a value of 1 to 19;
each c is independently an integer having a value of 3 to 8;
e, f, g, and p are each independently integers having a value of 0 or 1;
each n is independently an integer having a value of 0 to 3; and with the condition that the $X_a \text{BX}_b (\text{BX}_c)_n$ is a sequence having a maximum of 22 amino acid residues; and
c) a polypeptide represented by the general formula (II) (SEQ ID NO: 11):

$$C_f \text{ALCRALIKRIQA} \Delta \Omega \text{IPKGG-} \\ \text{R} \Omega \text{LPQLVCRLVL} \Phi \text{CS}_f \qquad (II)$$

wherein:
$\Delta$ is an amino acid residue independently selected from the group consisting of W and L;
each $\Omega$ is independently an amino acid residue selected from the group consisting of M, I, L, and nL;
$\Phi$ is an amino acid residue independently selected from the group consisting of R and T, preferably R; and
each f is independently an integer having a value of 0 or 1, wherein F, G, I, P, S, V, H, L, K, R, A, C, Q, W, Y, M, and T are standard one-letter symbols for amino acid residues, nL represents an L-nor-leucine residue, and Orn represents an L-onithine residue.

The present invention also provides pharmaceutically acceptable salts of said polypeptides and their blocked N- and/or C-terminus derivatives, e.g via acetylation and amidation.

The present invention also provides pharmaceutical compositions which contain such a reconstituted surfactant.

The present invention also provides methods for improving the alveolar patency at the end of expiration by administering such a reconstituted surfactant.

The present invention also provides methods for the prophylaxis and/or treatment of respiratory distress syndrome (RDS) and other respiratory disorders, by administering to a patient in need of such treatment a therapeutically effective amount of a reconstituted surfactant comprising a lipid carrier, a polypeptide of general formula (I), and a polypeptide of general formula (II).

In particular it has been found that, in a model of RDS wherein the immature newborn were treated with exogenous surfactant preparations without applying PEEP, a combination of said particular analogues of the proteins SP-C and SP-B acts on the lung gas volumes which is an index of the alveolar patency at the end of expiration.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the sequence of human protein SP-C. The Cys residues are palmitoylated in native SP-C. FIG. 1 discloses SEQ ID NO: 17.

FIG. 2 shows the sequence of human protein SP-B. FIG. 2 discloses SEQ ID NO: 18.

DETAILED DESCRIPTION OF THE PREFERRED EMBODIMENTS

Figure 3:
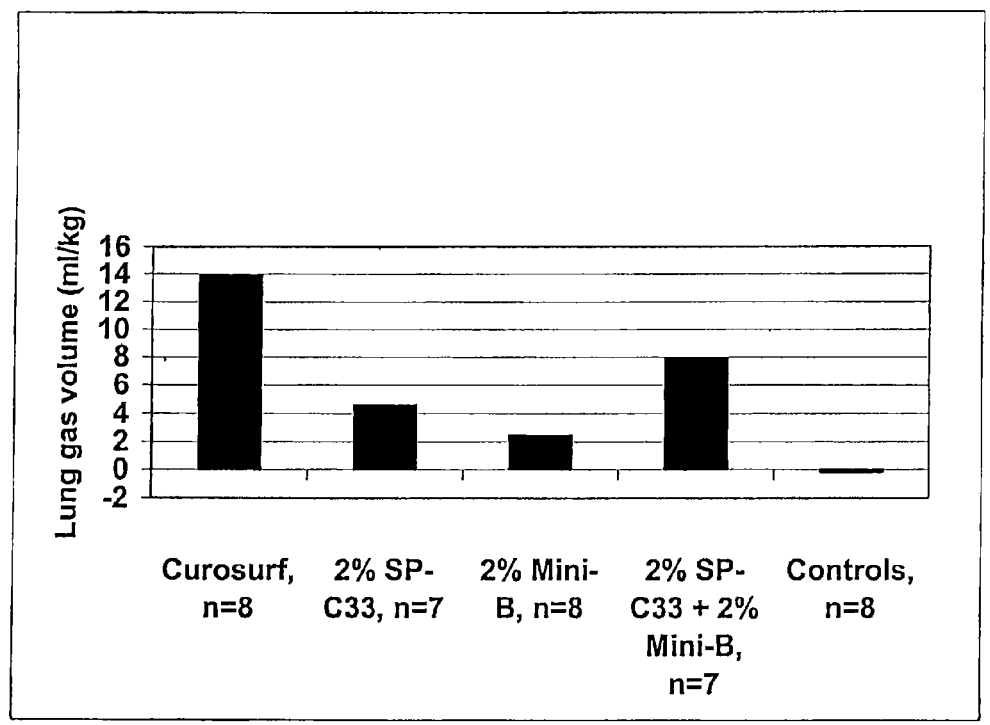
FIG. 3 shows certain results in terms of lung gas volumes (ml/kg).

The respiratory function after in vivo treatment with the exogenous surfactant preparations is carried out by measuring two parameters:
i) the tidal volume which is an index of the lung compliance and
ii) the lung gas volume which is an index of the alveolar air expansion or patency at the end of expiration, and, hence, of the capability of forming a stable phospholipidic film in the alveoli at the end of expiration.

In the present application, the term "reconstituted surfactant" means a lipid carrier to which polypeptide analogues of the surfactant proteins, made through recombinant technology or synthetic methods, have been added.

The term "lipid carrier" means a mixture of phosholipids and optionally further lipid components, for example neutral lipids such as triacylglycerols, free fatty acids, and/or cholesterol.

The term "polypeptide analogues of the native surfactant protein SP-C", includes polypeptides having an amino acid sequence in which, compared to the native proteins, one or more amino acids are missing or have been replaced by other amino acids, so long as the polypeptides, in a mixture with a lipid carrier, show pulmonary surfactant activity.

The term "polypeptide analogues of the native surfactant protein SP-B", includes peptides having an amino acid sequence in which, compared to the native proteins, one or more amino acids are missing so long as the polypeptides, in a mixture with a lipid carrier, show pulmonary surfactant activity.

The term "mini-B" means a 34-residue polypeptide based on the N-terminal residues 8-25 and C-terminal residues 63-78 of the native SP-B protein whose structure was first generically disclosed in a presentation taken from the California NanoSystems Institute website. Its full sequence has been subsequently disclosed in the RCSB Protein Data Bank. In A. J. Waring, et al., *J. Peptide Res.*, 2005, 66, 364-374, more information about its structure and activity has been reported.

The term "variants" means polypeptide analogues of the Mini-B peptide having an amino acid sequence in which one or more amino acids have been replaced by other amino acids, so long as the peptides, in a mixture with a lipid carrier, retain the activity of Mini-B.

The amino acid sequences are shown according to the single-letter or three-letter code with the amino acid which carries the free amino group at the left end (amino terminus) and the amino acid which carries the free carboxyl group at the right end (carboxy terminus).

The term "synergistic" means that the effectiveness of the two polypeptides is more than would be expected by summing their respective individual effectiveness in a given assay.

All the amino acid residues identified herein are in the natural L-configuration and the sequences identified herein are reported according to standard abbreviations for amino acid residues as shown in the following Table of Correspondence.

Table of Correspondence

| Amino Acid | Symbol | |
|---|---|---|
| | One Letter | Three Letter |
| Glycine | G | Gly |
| L-proline | P | Pro |
| L-isoleucine | I | Ile |
| L-leucine | L | Leu |
| L-tyrosine | Y | Tyr |
| L-cysteine | C | Cys |
| L-tryptophan | W | Trp |
| L-alanine | A | Ala |
| L-lysine | K | Lys |
| L-arginine | R | Arg |
| L-glutamine | Q | Glu |
| L-methionine | M | Met |
| L-serine | S | Ser |
| L-valine | V | Val |
| L-aspargine | N | Asn |
| L-aspartic acid | D | Asp |
| L-glutamic acid | E | Gln |
| L-histidine | H | His |
| L-threonine | T | Thr |
| L-phenylalanine | F | Phe |
| L-nor-leucine | — | nLeu |
| L-omithine | — | Orn |

Thus, the present invention provides reconstituted surfactants comprising a lipid carrier and a combination of particular polypeptide analogues of the native surfactant protein SP-C with particular polypeptide analogues of the native surfactant protein SP-B, including the Mini-B peptide and variants thereof.

It has been found that, in a model of RDS wherein the immature newborn were treated with exogenous surfactant preparations without applying PEEP, a combination of a polypeptide of general formula (I), with a polypeptide of general formula (II) positively acts on the lung compliance. In particular, the combination of the two polypeptides was found to act in a synergistic way on the lung gas volumes which is an index of the alveolar patency at the end of expiration. Said result demonstrates that the reconstituted surfactant of the present invention is able to stabilise the phospholipid film in the alveoli at the end of expiration in a better way than a reconstituted surfactant comprising only an analog of the protein SP-C or an analog of the protein SP-B.

Moreover, the claimed reconstituted surfactant preparation also improved the respiratory function as expressed by the tidal volumes to an extent comparable or even slightly better than that achieved after administration of a modified natural surfactant.

Advantageously the analog of the native protein SP-C is a polypeptide of at least 20 amino acid residues and no more than 40 amino acid residues, having the sequence represented by the general formula (I) SEQ ID NO: 10:

$$F_e G_e I_f P_f S_g SPVHLKRX_a BX_b (BX_c)_n GALL\Omega_p G_p L_p \qquad (I)$$

wherein:
each X is independently an amino acid residue selected from the group consisting of I, L, and nL;
each B is independently an amino acid residue selected from the group consisting of K, R, H, W, F, Y, and Orn;
each S is independently optionally substituted with an acyl group containing 12-22 carbon atoms, preferably 16 carbon atoms, linked to the side chain via an ester bond;
$\Omega$ is an amino acid residue selected from the group consisting of M or its oxidized on the sulfur atom, I, L, and nL;
a is an integer having a value of 1 to 8;
b is an integer having a value of 1 to 19;
each c is independently an integer having a value of 3 to 8;
e, f, g and p are each independently integers having a value of 0 or 1;
n is an integer having a value comprised from 0 to 3; and
with the condition that the $X_a BX_b (BX_c)_n$ is a sequence having a maximum of 22 amino acids, preferably comprised between 10 and 22 amino acid residues.

Preferably the polypeptide of general formula (I) is constituted of at least 30 and not more than 35 amino acid residues, more preferably not more than 33 amino acid residues.

In particular embodiments, the polypeptides of general formula (I) are constituted of 30 or 33 or 35 amino acid residues.

Preferably the polypeptide analog of the SP-C protein is represented by the general formula (Ia) (SEQ ID NO: 13) in which e and n are 0, and g is 1:

$$I_f P_f SSPVHLKRX_a BX_b GALL\Omega_p G_p L_p \qquad (Ia)$$

wherein
X, B, and $\Omega$ are as defined above;
a is from 1 to 8, preferably from 1 to 3; more preferably 1;
b is from 1 to 19, preferably from 5 to 15; more preferably 14; and
each f and p are independently 0 or 1.

More preferably the polypeptide analog of the SP-C protein is represented by the general formula (Ib) (SEQ ID NO: 14) in which f is 1:

$$IPSSPVHLKRX_a BX_b GALL\Omega_p G_p L_p \qquad (Ib)$$

wherein:
X, B, $\Omega$, a, and b are as defined above; and
each p is independently 0 or 1.

Even more preferably, the polypeptide analog of the SP-C protein is represented by the general formula (Ic) (SEQ ID NO: 15):

$$IPSSPVHLKRLKLLLLLLLILLLILGALL\Omega_p G_p L_p \qquad (Ic)$$

wherein:
$\Omega$ is as defined above
each p is independently 0 or 1.

Examples of polypeptides of formula (Ic) are reported below:

```
                                        (SEQ ID NO: 1)
IPSSPVHLKRLKLLLLLLLILLLILGALLMGL     (Id)

(SEQ ID NO: 2)
IPSSPVHLKRLKLLLLLLLILLLILGALLIGL     (Ie)
```

-continued

IPSSPVHLKRLKLLLLLLLLILLLILGALLLGL (If) (SEQ ID NO: 3)

IPSSPVHLKRLKLLLLLLLLILLLILGALLnLGL (Ig) (SEQ ID NO: 4)

IPSSPVHLKRLKLLLLLLLLILLLILGALL (Ih). (SEQ ID NO: 5)

The polypeptide (Id) has been also referred to in the prior art as SP-C33.

Most preferably the SP-C analog is a polypeptide selected from the group of polypeptides having the formulae (Ie), (If), (Ig), and (Ih).

In a preferred embodiment of the invention, the polypeptide of general formula (I) is the polypeptide (If) hereinafter referred to as SP-C33(Leu)$^{31}$.

Advantageously, the analog of the native protein SP-B consists of two portions corresponding to the N-terminal residues 8-25 and to the 63-78 C-terminal part of the native SP-B protein (referred to as Mini-B peptide) or a variant thereof.

More advantageously, the analog of the native protein SP-B is a polypeptide represented by the following general formula (II) (SEQ ID NO: 11):

C$_f$ALCRALIKRIQAΩIPKGG-RΩLPQLVCRLVLΦCS$_f$ (II)

wherein:
  Δ is an amino acid residue selected form the group consisting of W and L;
  each Ω is independently an amino acid residue independently selected from the group consisting of M, I, L, and nL;
  Φ is an amino acid residue selected from the group consisting of R and T, preferably R; and
  each f is independently an integer having a value of 0 or 1.

In a particular embodiment of the invention, the SP-B analog is a polypeptide represented by the formula (IIa) (SEQ ID NO: 6):

CWLCRALIKRIQAMIPKGGRMLPQLVCR-LVLRCS (IIa).

In another embodiment of the invention, the SP-B analog is selected from those having the following formulae:

CLLCRALIKRIQAMIPKGGRMLPQLVC-RLVLRCS (IIb) (SEQ ID NO: 7)

CWLCRALIKRIQALIPKGGRLLPQLVC-RLVLRCS (IIc) (SEQ ID NO: 8)

CLLCRALIKRIQALIPKGGRLLPQLVC-RLVLRCS (IId) (SEQ ID NO: 9).

In a preferred embodiment, each of the polypeptides (IIa), (IIb), (IIc), and (IId) may be in the form of a disulfide-linked molecule, wherein the intramolecular disulfide linkage is between the two Cys residues in position 1 and 33 and/or between the two Cys residues in position 4 and 27.

The disulfide linked polypeptide (IIa) has been referred to in the art to as oxidized Mini-B (ox Mini-B).

The polypeptide (IIc) is hereinafter referred to as Mini-B (Leu) and its disulfide linked form as ox Mini-B(Leu).

The polypeptides of general formulae (I) and (II) may be prepared according to synthetic methods or recombinant techniques well known to the person skilled in the art. An excellent summary of the many techniques available may be found in J. M. Steward and J. D. Young, "Solid Phase Peptide Synthesis," W.H. Freeman Co., San Francisco, 1969; and J. Meienhofer, "Hormonal Proteins and Peptides," Vol. 2, p. 46, Academic Press (New York), 1983, for solid phase peptide synthesis; and in E. Schroder and K. Kubke, "The Peptides," Vol. 1, Academic Press (New York), 1965, for classical solution synthesis.

The polypeptides of the present invention can also be prepared using the solid-phase synthetic technique initially described by Merrifield, in J. Am. Chem. Soc., 85: 2149-2154 (1963). Other polypeptide synthesis techniques may be found, for example, in M. Bodanszky et al., "Peptide Synthesis: John Wiley & Sons, 2d Ed., (1976) as well as in other reference works known to those skilled in the art.

Appropriate protective groups for use in such syntheses will be found in the above texts as well as in J. F. W. McOmie, "Protective Groups in Organic Chemistry," Plenum Press, New York, N.Y. (1973).

For example, the polypeptides of general formula (I) may be prepared according to the method disclosed in WO 00/47623, while the polypeptides of general formula (II) may be prepared according to the method reported in A. J. Waring, et al., J. Peptide Res., 2005, 66, 364-374.

The present invention also provides the pharmaceutically acceptable salts of the polypeptides of general formulae (I) and (II) and their blocked N- and/or C-terminus derivatives, e.g., via acetylation and amidation. Pharmaceutically acceptable salts include for example, salts of hydrochloric acid, acetic acid, and trifluoroacetic acid.

The reconstituted surfactant of the present invention may be prepared by mixing a solution or a suspension of the polypeptides of general formula (I) and (II) and lipids and by subsequently drying the mixture, otherwise they may be prepared by lyophilisation or spray-drying.

Preferably, the polypeptides of general formula (I) and the polypeptides of general formula (II) are present in the reconstituted surfactants of the invention in a fixed amount and quantitative ratio as a fixed combination.

The proportion of the polypeptides of general formulae (I) and (II) relative to the reconstituted surfactant can vary. Advantageously each polypeptide may be present in an amount of 0.5 to 10 wt. % based on the total weight of the surfactant (w/w), preferably 1 to 5 wt. %, most preferably 1 to 3 wt. %.

In a preferred embodiment, the reconstituted surfactant comprises 1 to 3% by weight of the polypeptide (If), and 1 to 3% by weight of the polypeptide (IIa), preferably in the oxidized form.

In another preferred embodiment, the reconstituted surfactant comprises 1 to 3% by weight of the polypeptide (If), and 1 to 3% by weight of the polypeptide (IIc), preferably in the oxidized form.

Advantageously, the lipid carrier comprises the phospholipids that are contained in natural pulmonary surfactant preparations, for example phosphatidylcholines (PC) such as dipalmitoylphosphatidylcholine (DPPC) and palmitoyloleoylphosphatidylcholine (POPC), and phosphatidylglycerols (PG), such as palmitoyloleoylphosphatidylglycerol (POPG) and dipalmitoylphosphatidylglycerol (DPPG).

Other phospholipids which can be advantageously used are phosphatidylinositols (PI), phosphatidylethanolamines (PE), phosphatidylserines, and sphingomyelins (SM).

In a particular embodiment, the lipid carrier may comprise further components, for example neutral lipids such as triacylglycerols, free fatty acids, and/or cholesterol.

Advantageously the reconstituted surfactant according to the present invention comprises 90 to 99% by weight of a lipid carrier, preferably 92 to 98% by weight, more preferably 94 to 96% by weight, and 1 to 10% by weight of the sum of both peptides, preferably 2 to 8% by weight, more preferably 4 to 6% weight, based on the total weight of the lipid and the polypeptides of formulae (I) and (II).

In one of the embodiments of the present invention, the reconstituted surfactant comprises about 96% by weight of a lipid carrier, about 2% by weight of a polypeptide of general formula (I) and about 2% by weight of a polypeptide of general formula (II).

In a particular embodiment, the lipid carried only consists of phospholipids more preferably of a mixture of: (1) DPPC; and (2) a palmitoyloleylphospholipid selected from POPG or a mixture thereof with POPC in weight ratios ranging from 95:5 to 50:50, preferably from 80:20 to 60:40.

The weight ratio between DPPC and POPG ranges preferably from 75:25 to 65:35, and is more preferably about 68:31. In the case of DPPC:POPG:POPC mixtures, the phospholipids are preferably used in weight ratios of about 60:20:20 or about 68:15:16.

In another embodiment, the lipid carrier may consist of DPPC, DPPG, and cholesterol.

In a preferred embodiment of the invention, the reconstituted surfactant comprises from 1 to 5% by weight of one the polypeptides of general formula (Ia), from 1 to 5% by weight of one of the polypeptides of general formula (II) and a mixture of DPPC and POPG in a weight ratio of about 68:31.

The administration of the reconstituted surfactant of the invention is carried out in a manner known to the person skilled in the art, preferably by intratracheal installation (infusion or bolus) or by nebulisation.

The present invention also provides pharmaceutical compositions comprising the reconstituted surfactant of the invention. Said compositions are advantageously administered in the form of a solution, dispersion, suspension, or dry powder. Preferably said compositions comprise the reconstituted surfactant dissolved or suspended in a suitable solvent or resuspension medium.

Preferably said pharmaceutical compositions are supplied as suspension in a buffered physiological saline aqueous solution in single-use glass vials. Advantageously, the reconstituted surfactant concentration (expressed as phospholipid content) is in the range of from about 2 to about 160 mg of surfactant per ml, preferably between 10 and 100 mg/ml, more preferably between 20 and 80 mg/ml.

Said compositions may further comprise electrolytes, such as calcium, magnesium and/or sodium salts, preferably calcium chloride.

The pharmaceutical compositions according to the present invention are suitable for the prophylaxis and/or treatment of respiratory distress syndrome (RDS) in prematurely born babies or other diseases related to a surfactant-deficiency or dysfunction including RDS in adults (ARDS), meconium aspiration syndrome (MAS), and bronchopulmonary dysplasia (BPD).

The present reconstituted surfactants may also be useful for the prophylaxis and/or treatment of other respiratory disorders such as pneumonia, bronchitis, COPD (chronic obstructive pulmonary disease), asthma, and cystic fibrosis as well as for the treatment of serous otitis media (glue ear).

Other features of the invention will become apparent in the course of the following descriptions of exemplary embodiments which are given for illustration of the invention and are not intended to be limiting thereof.

EXAMPLES

Example 1

Synthesis and Purification of the Polypeptides SP-C33(Leu)$^{31}$ and SP-C33

The polypeptide SP-C33(Leu)$^{31}$ was prepared by standard SPPS (Solid Phase Peptide Synthesis) methods based on Fmoc chemistry and consecutive TFA-cleavages. In total 186.0 g of crude SP-C33(Leu)$^{31}$ were obtained. The polypeptide was purified by subjecting the material to counter current distribution (CCD) using $H_2O$/n-BuOH/AcOEt/AcOH 4:1:4:1 as a biphasic solvent system. This purification yielded 78.9 g of SP-C33(Leu)$^{31}$ with a purity of >60%. The final purification was carried out by preparative HPLC using PLRP-S as the stationary phase in a steel column of 50×300 mm applying a linear gradient of 25% B to 100% B in 75 minutes. The mobile phase consisted of buffer A=0.1% TFA in ACN/$H_2O$ 1:4 and buffer B=0.1% TFA in IPA. The purified polypeptide was dissolved in 90% AcOH and passed through a column packed with Dowex ion exchange resin (acetate form) to furnish, after lyophilisation, 5.8 g (=5.4%) of the final product as the acetate.

The polypeptide SP-C33 was prepared in an analogous manner.

Legend:
ACN Acetonitrile
AcOEt Ethyl acetate
AcOH Acetic acid
Boc t-Butyloxycarbonyl
n-BuOH n-Butanol
Fmoc 9-Fluorenylmethyloxycarbonyl
IPA Isopropyl alcohol
TFA Trifluoroacetic acid Example 2

Synthesis and Purification of the Polypeptides ox Mini-B(Leu) and ox-Mini-B

The polypeptide ox-Mini-B(Leu) was prepared by standard SPAS (Solid Phase Peptide Synthesis) methods based on Fmoc chemistry and consecutive TFA-cleavages. The crude polypeptide was purified with preparative HPLC using a TFA system and isolated by lyophilisation. Air oxidation of the purified peptide yielded the monocyclic sequence with the disulfide bond between $Cys^1$ and $Cys^{33}$. The monocyclic peptide was purified with preparative HPLC using a TFA system and isolated by lyophilisation. The second disulfide bridge between $Cys^4$ and $Cys^{27}$ was formed using iodine. After oxidation, the product was purified with preparative HPLC using a TFA system and isolated by lyophilisation. 1.12 g (=1.7%) of the final compound were isolated with a purity of >89%.

The polypeptide ox Mini-B was prepared in an analogous manner.

Example 3

In Vivo Experiments with a Reconstituted Surfactant Based on Ox Mini-B and SP-C33

The surfactant preparations were assayed in premature newborn rabbits, obtained by hysterectomy at the gestational age of 27 days. The experiments were performed without applying a positive end expiratory pressure (PEEP). As the SP-C analog, the polypeptide referred to as SP-C33 was used which was prepared according to Example 1. As the analog of the protein SP-B, oxidized Mini-B (ox Mini-B) was used which was prepared according to Example 2.

The animals were treated at birth with reconstituted surfactant preparations containing, as lipid carrier, the phospholipid mixture DPPC:POPG in the ratio 68:31 w/w. The phospholipids were mixed with 2 or 4% w/w SPC-33, 2% w/w ox Mini-B, or 2% w/w SPC-33 plus 2% w/w ox Mini-B. Animals receiving the same dose of Curosurf® served as positive controls, and non-treated littermates served as negative controls. All surfactant preparations were administered at a concentration of 80 mg/ml and at a standard dose of 2.5 ml/kg.

The immature newborn rabbits were ventilated in parallel with a standardized sequence of peak insufflation pressures. To open up the lungs, pressure was first set at 35 cmH$_2$O for 1 minute. After this recruitment manoeuvre, pressure was lowered to 25 cmH$_2$O for 15 minutes and further on to 20 and 15 cm H$_2$O. Finally, the pressure was raised again to 25 cmH$_2$O for 5 minutes, after which the lungs were ventilated for additional 5 minutes with nitrogen and then excised for gas volume measurements. Both lung gas volumes and tidal volumes expressed as ml/kg were measured, and the results, given as median values, are reported in FIGS. 3 and 4, respectively.

From FIG. 3 it can be appreciated that animals treated with the reconstituted surfactant preparation containing 2% w/w ox Mini-B had lower lung gas volumes than animals that received 2% w/w SP-C33 (about 2 ml/kg vs about 4 ml/kg). Addition of 2% w/w ox Mini-B to SP-C33 surfactant produced a significantly greater increment in lung gas volumes than either peptide alone (8 ml/kg vs about 6 ml/kg).

Figure 4:
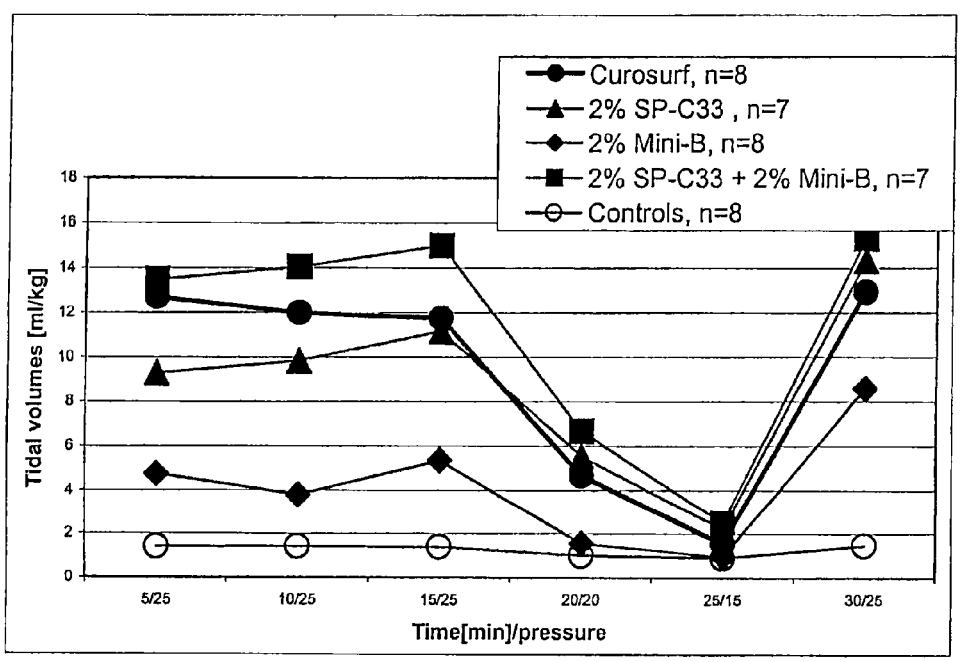
FIG. 4 shows certain results in terms of tidal volumes (ml/kg) as a function of time/pressure.

As shown in FIG. 4, a similar trend was observed for the tidal volumes and, after administration of the peptides in combination an improvement comparable or even slightly better than that achieved after administration of Curosurf® was observed. It has also been found that the increase of SP-C33 content form 2 to 4% w/w did not increase lung gas volumes indicating that the stabilising effect of the phospholipid film in the alveoli at the end of expiration is due to the addition of ox Mini-B. Said result demonstrates that the reconstituted surfactant of the invention is able to stabilise the phosholipid film in the alveoli at the end of expiration in a better way than the reconstituted surfactants comprising only an analog of the protein SP-C or only an analog of the protein SP-B. Moreover, the reconstituted surfactant preparation according to the present invention turned out to improve the respiratory function as expressed by the tidal volumes to an extent comparable or even slightly better than that achieved after administration of a modified natural surfactant.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A reconstituted surfactant, comprising:
   (a) a lipid carrier;
   (b) at least one polypeptide represented by formula (Ic) (SEQ ID NO: 15):

IPSSPVHLKRLKLLLLLLLLILLLILGALL$\Omega_p G_p L_p$   (Ic)

wherein:
   $\Omega$ is an amino acid residue selected from the group consisting of M, M which is oxidized at the sulfur atom, I, L, and nL; and
   each p is independently 0 or 1,
   or at least one pharmaceutically acceptable salt thereof, or at least one blocked N- and/or C-terminus derivative thereof; and
   (c) at least one polypeptide represented by formula (II) (SEQ ID NO: 11):

C$_f$ALCRALIKRIQA$\Omega$IPKGG-R$\Omega$LPQLVCRLVL$\Phi$CS$_f$   (II)

wherein:
   $\Delta$ is W;
   each $\Omega$ is independently an amino acid residue selected from the group consisting of M, I, L, and nL;
   $\Phi$ is R; and
   f is 1,
   or at least one pharmaceutically acceptable salt thereof, or at least one blocked N- and/or C-terminus derivative thereof,
   wherein said polypeptide represented by formula (II) is in the form of disulfide linked molecule with intramolecular disulfide linkages between the two Cys residues in position 1 and 33 and between the two Cys residues in position 4 and 27, and
   wherein said lipid carrier comprises a mixture of phospholipids.

2. A reconstituted surfactant according to claim 1, wherein said at least one polypeptide represented by formula (Ic), pharmaceutically acceptable salt thereof, or blocked N- and/or C-terminus derivative thereof and said at least one polypeptide represented by formula (II), pharmaceutically acceptable salt thereof, or blocked N- and/or C-terminus derivative thereof are each present in an amount of 0.5 to 10 wt. %, based on the total weight of the surfactant.

3. A reconstituted surfactant according to claim 1, which comprises at least one polypeptide represented by formula (IIa) (SEQ ID NO: 6):

CWLCRALIKRIQAMIPKGGRMLPQLVCR-LVLRCS   (IIa), or at least one pharmaceutically acceptable salt thereof, or at least one blocked N- and/or C-terminus derivative thereof, which is in the form of disulfide linked molecule with intramolecular disulfide linkages between the two Cys residues in position 1 and 33 and between the two Cys residues in position 4 and 27.

4. A reconstituted surfactant according to claim 1, which comprises at least one polypeptide selected from the group consisting of:

IPSSPVHLKRLKLLLLLLLLILLLILGALLMGL   (SEQ ID NO: 1) (Id),
   IPSSPVHLKRLKLLLLLLLLILLLILGALLIGL   (SEQ ID NO: 2) (Ie),
   IPSSPVHLKRLKLLLLLLLLILLLILGALLLGL   (SEQ ID NO: 3) (If),
   IPSSPVHLKRLKLLLLLLLLILLLILGALLnLGL   (SEQ ID NO: 4) (Ig),
   IPSSPVHLKRLKLLLLLLLLILLLILGALL   (SEQ ID NO: 5) (Ih), a pharmaceutically acceptable salt thereof, or a blocked N- and/or C-terminus derivative thereof.

5. A reconstituted surfactant according to claim 1, which comprises:
   a polypeptide represented by formula (If) (SEQ ID NO: 3):

IPSSPVHLKRLKLLLLLLLLILLLILGALLLGL   (If), a pharmaceutically acceptable salt thereof, or a blocked N- and/or C-terminus derivative thereof; and
   a polypeptide represented by formula (IIa) (SEQ ID NO: 6):

CWLCRALIKRIQAMIPKGGRMLPQLVCR-LVLRCS   (IIa), a pharmaceutically acceptable salt thereof, or a blocked N- and/or C-terminus derivative thereof,
   which is in the form of disulfide linked molecule with intramolecular disulfide linkages between the two Cys residues in position 1 and 33 and between the two Cys residues in position 4 and 27.

6. A reconstituted surfactant according to claim 1, which comprises:
   a polypeptide represented by formula (If) (SEQ ID NO: 3):

IPSSPVHLKRLKLLLLLLLLILLLILGALLLGL   (If), a pharmaceutically acceptable salt thereof, or a blocked N- and/or C-terminus derivative thereof; and
   a polypeptide represented by formula (IIc) (SEQ ID NO: 8):

CWLCRALIKRIQALIPKGGRLLPQLVCRLVLRCS   (IIc), a one pharmaceutically acceptable salt thereof, or a blocked N- and/or C-terminus derivative thereof,
   which is in the form of disulfide linked molecule with intramolecular disulfide linkages between the two Cys residues in position 1 and 33 and between the two Cys residues in position 4 and 27.

7. A reconstituted surfactant according to claim 1, wherein said mixture of phospholipids consists of dipalmitoyl phosphatidylcholine and a palmitoyl oleoyl phospholipid selected from the group consisting of palmitoyl oleoyl phosphatidylglycerol, and a mixture of palmitoyl oleoyl phosphatidylglycerol with palmitoyl oleoyl phosphatidylcholine in weight ratios ranging from 95:5 to 50:50.

8. A reconstituted surfactant according to claim 1, wherein said mixture of phospholipids mixture consists of dipalmitoyl phosphatidylcholine and palmitoyl oleoyl phosphatidylglycerol in a weight ratio of about 68:31.

9. A pharmaceutical composition, comprising a reconstituted surfactant according to claim 1.

10. A pharmaceutical composition according to claim 9, which is in the form of either a solution, a dispersion, a suspension, or a dry powder.

11. A pharmaceutical composition according to claim 10, which is in the form of aqueous suspension.

12. A pharmaceutical composition according to claim 11, which comprises said reconstituted surfactant in a concentration of 2 to 160 mg/ml.

13. A pharmaceutical composition according to claim 12, which comprises said reconstituted surfactant in a concentration of 20 to 80 mg/ml.

14. A reconstituted surfactant according to claim 1, which, when administered to a subject for the treatment or prophylaxis of a disease related to a surfactant deficiency or dysfunction, affords a lung gas volume which is greater than that afforded by:
    (1) administration of a reconstituted surfactant which comprises (a) said lipid carrier and (b) said at least one polypeptide represented by formula (Ic) (SEQ ID NO: 15) but no (c) said at least one polypeptide represented by formula (II) (SEQ ID NO: 11); and
    (2) administration of a reconstituted surfactant which comprises (a) said lipid carrier and (c) said at least one polypeptide represented by formula (II) (SEQ ID NO: 11) but no (b) said at least one polypeptide represented by formula (Ic) (SEQ ID NO: 15).

15. A method for the treatment and/or prophylaxis of respiratory distress syndrome (RDS) in a prematurely born baby, comprising administering an effective amount of a reconstituted surfactant according to claim 1 to said prematurely born baby.

16. A method for the treatment or prophylaxis of a disease related to a surfactant deficiency or dysfunction, comprising administering an effective amount of a reconstituted surfactant according to claim 1 to a subject in need thereof.

17. The method according to claim 16, wherein said disease related to a surfactant deficiency or dysfunction is selected from the group consisting of RDS in an adult, meconium aspiration syndrome, and bronchopulmonary dysplasia.

18. A method according to claim 15, which affords a lung gas volume which is greater than that afforded by:
    (1) administration of a reconstituted surfactant which comprises (a) said lipid carrier and (b) said at least one polypeptide represented by formula (Ic) (SEQ ID NO: 15) but no (c) said at least one polypeptide represented by formula (II) (SEQ ID NO: 11); and
    (2) administration of a reconstituted surfactant which comprises (a) said lipid carrier and (c) said at least one polypeptide represented by formula (II) (SEQ ID NO: 11) but no (b) said at least one polypeptide represented by formula (Ic) (SEQ ID NO: 15).

19. A method according to claim 16, which affords a lung gas volume which is greater than that afforded by:
    (1) administration of a reconstituted surfactant which comprises (a) said lipid carrier and (b) said at least one polypeptide represented by formula (Ic) (SEQ ID NO: 15) but no (c) said at least one polypeptide represented by formula (II) (SEQ ID NO: 11); and
    (2) administration of a reconstituted surfactant which comprises (a) said lipid carrier and (c) said at least one polypeptide represented by formula (II) (SEQ ID NO: 11) but no (b) said at least one polypeptide represented by formula (Ic) (SEQ ID NO: 15).

20. A method according to claim 17, which affords a lung gas volume which is greater than that afforded by:
    (1) administration of a reconstituted surfactant which comprises (a) said lipid carrier and (b) said at least one polypeptide represented by formula (Ic) (SEQ ID NO: 15) but no (c) said at least one polypeptide represented by formula (II) (SEQ ID NO: 11); and
    (2) administration of a reconstituted surfactant which comprises (a) said lipid carrier and (c) said at least one polypeptide represented by formula (II) (SEQ ID NO: 11) but no (b) said at least one polypeptide represented by formula (Ic) (SEQ ID NO: 15).

\* \* \* \* \*

SEQUENCE LISTING

```
<160> NUMBER OF SEQ ID NOS: 18

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25                  30

Leu

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Ile Gly
            20                  25                  30

Leu
```

```
<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Leu Gly
            20                  25                  30

Leu

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any amino acid
<220> FEATURE:
<223> OTHER INFORMATION: see specification as filed for detailed
      description of substitutions and preferred embodiments

<400> SEQUENCE: 4

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Leu
            20                  25                  30

Gly Leu

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu
            20                  25                  30

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser
```

```
<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Cys Leu Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Cys Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Cys Leu Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser

<210> SEQ ID NO 10
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(5)
<223> OTHER INFORMATION: May or may not be present
<220> FEATURE:
<221> NAME/KEY: MOD_RES
<222> LOCATION: (13)..(20)
<223> OTHER INFORMATION: Ile, Leu or nor-leucine and this region may
      encompass 1 to 8 residues
<220> FEATURE:
<221> NAME/KEY: MOD_RES
<222> LOCATION: (21)..(21)
<223> OTHER INFORMATION: Lys, Arg, His, Trp, Phe, Tyr or Ornithine
```

-continued

```
<220> FEATURE:
<221> NAME/KEY: MOD_RES
<222> LOCATION: (22)..(40)
<223> OTHER INFORMATION: Ile, Leu or nor-leucine and this region may
      encompass 1 to 19 residues
<220> FEATURE:
<221> NAME/KEY: MOD_RES
<222> LOCATION: (41)..(41)
<223> OTHER INFORMATION: Lys, Arg, His, Trp, Phe, Tyr or Ornithine
<220> FEATURE:
<221> NAME/KEY: MOD_RES
<222> LOCATION: (42)..(49)
<223> OTHER INFORMATION: Ile, Leu, or nor-leucine and this region may
      encompass 3 to 8 residues
<220> FEATURE:
<221> NAME/KEY: MOD_RES
<222> LOCATION: (50)..(50)
<223> OTHER INFORMATION: Lys, Arg, His, Trp, Phe, Tyr or Ornithine
<220> FEATURE:
<221> NAME/KEY: MOD_RES
<222> LOCATION: (51)..(58)
<223> OTHER INFORMATION: Ile, Leu or nor-leucine and this region may
      encompass 3 to 8 residues
<220> FEATURE:
<221> NAME/KEY: MOD_RES
<222> LOCATION: (59)..(59)
<223> OTHER INFORMATION: Lys, Arg, His, Trp, Phe, Tyr or Ornithine
<220> FEATURE:
<221> NAME/KEY: MOD_RES
<222> LOCATION: (60)..(67)
<223> OTHER INFORMATION: Ile, Leu or nor-leucine and this region may
      encompass 3 to 8 residues
<220> FEATURE:
<221> NAME/KEY: misc_feature
<222> LOCATION: (41)..(67)
<223> OTHER INFORMATION: This region may encompass 0 to 3 4-9 residue
      repeating units
<220> FEATURE:
<221> NAME/KEY: MOD_RES
<222> LOCATION: (71)..(73)
<223> OTHER INFORMATION: This region may encompass 0 to 3 residues
<220> FEATURE:
<221> NAME/KEY: MOD_RES
<222> LOCATION: (74)..(74)
<223> OTHER INFORMATION: Met, Met oxidized on the sulfur atom, Ile, Leu,
      nor-leucine and may or may not be present
<220> FEATURE:
<221> NAME/KEY: MOD_RES
<222> LOCATION: (75)..(76)
<223> OTHER INFORMATION: May or may not be present
<220> FEATURE:
<223> OTHER INFORMATION: see specification as filed for detailed
      description of substitutions and preferred embodiments

<400> SEQUENCE: 10

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Gly Ala Leu Leu Leu Leu Xaa Gly Leu
65                  70                  75

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Trp or Leu
<220> FEATURE:
<221> NAME/KEY: MOD_RES
<222> LOCATION: (14)..(14)
<223> OTHER INFORMATION: Met, Ile, Leu or nor-leucine
<220> FEATURE:
<221> NAME/KEY: MOD_RES
<222> LOCATION: (21)..(21)
<223> OTHER INFORMATION: Met, Ile, Leu or nor-leucine
<220> FEATURE:
<221> NAME/KEY: MOD_RES
<222> LOCATION: (32)..(32)
<223> OTHER INFORMATION: Arg or Thr
<220> FEATURE:
<221> NAME/KEY: MOD_RES
<222> LOCATION: (34)..(34)
<223> OTHER INFORMATION: May or may not be present
<220> FEATURE:
<223> OTHER INFORMATION: see specification as filed for detailed
      description of substitutions and preferred embodiments

<400> SEQUENCE: 11

Cys Xaa Leu Cys Arg Ala Leu Ile Lys Arg Ile Gln Ala Xaa Ile Pro
1               5                   10                  15

Lys Gly Gly Arg Xaa Leu Pro Gln Leu Val Cys Arg Leu Val Leu Xaa
            20                  25                  30

Cys Ser

<210> SEQ ID NO 12
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(5)
<223> OTHER INFORMATION: May or may not be present
<220> FEATURE:
<221> NAME/KEY: MOD_RES
<222> LOCATION: (13)..(20)
<223> OTHER INFORMATION: Ile, Leu or nor-leucine and this region may
      encompass 1 to 8 residues
<220> FEATURE:
<221> NAME/KEY: MOD_RES
<222> LOCATION: (21)..(21)
<223> OTHER INFORMATION: Lys, Arg, His, Trp, Phe, Tyr and Ornithine
<220> FEATURE:
<221> NAME/KEY: MOD_RES
<222> LOCATION: (22)..(40)
<223> OTHER INFORMATION: Ile, Leu or nor-leucine and this region may
      encompass 1 to 19 residues
<220> FEATURE:
<221> NAME/KEY: MOD_RES
<222> LOCATION: (41)..(41)
<223> OTHER INFORMATION: Lys, Arg, His, Trp, Phe, Tyr and Ornithine
<220> FEATURE:
<221> NAME/KEY: MOD_RES
<222> LOCATION: (42)..(49)
<223> OTHER INFORMATION: Ile, Leu nor-leucine and this region may
      encompass 3 to 8 residues
<220> FEATURE:
<221> NAME/KEY: MOD_RES
<222> LOCATION: (50)..(50)
<223> OTHER INFORMATION: Lys, Arg, His, Trp, Phe, Tyr and Ornithine
```

```
<220> FEATURE:
<221> NAME/KEY: MOD_RES
<222> LOCATION: (51)..(58)
<223> OTHER INFORMATION: Ile, Leu nor-leucine and this region may
      encompass 3 to 8 residues
<220> FEATURE:
<221> NAME/KEY: MOD_RES
<222> LOCATION: (59)..(59)
<223> OTHER INFORMATION: Lys, Arg, His, Trp, Phe, Tyr and Ornithine
<220> FEATURE:
<221> NAME/KEY: MOD_RES
<222> LOCATION: (60)..(67)
<223> OTHER INFORMATION: Ile, Leu nor-leucine and this region may
      encompass 3 to 8 residues
<220> FEATURE:
<221> NAME/KEY: misc_feature
<222> LOCATION: (41)..(67)
<223> OTHER INFORMATION: This region may encompass 0 to 3 4-9 residue
      repeating units
<220> FEATURE:
<221> NAME/KEY: MOD_RES
<222> LOCATION: (72)..(72)
<223> OTHER INFORMATION: Met, Met oxidized on the sulfur atom, Ile, Leu,
      nor-leucine and may or may not be present
<220> FEATURE:
<221> NAME/KEY: MOD_RES
<222> LOCATION: (73)..(74)
<223> OTHER INFORMATION: May or may not be present
<220> FEATURE:
<223> OTHER INFORMATION: see specification as filed for detailed
      description of substitutions and preferred embodiments

<400> SEQUENCE: 12

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Gly Ala Leu Leu Xaa Gly Leu
65                  70

<210> SEQ ID NO 13
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: May or may not be present
<220> FEATURE:
<221> NAME/KEY: MOD_RES
<222> LOCATION: (11)..(18)
<223> OTHER INFORMATION: Ile, Leu or nor-leucine and this region may
      encompass 1 to 8 residues
<220> FEATURE:
<221> NAME/KEY: MOD_RES
<222> LOCATION: (19)..(19)
<223> OTHER INFORMATION: Lys, Arg, His, Trp, Phe, Tyr or Ornithine
<220> FEATURE:
<221> NAME/KEY: MOD_RES
<222> LOCATION: (20)..(38)
<223> OTHER INFORMATION: Ile, Leu or nor-leucine and this region may
      encompass 1 to 19 residues
```

```
<220> FEATURE:
<221> NAME/KEY: MOD_RES
<222> LOCATION: (43)..(43)
<223> OTHER INFORMATION: Met, Met oxidized on the sulfur atom, Ile, Leu,
      nor-leucine and may or may not be present
<220> FEATURE:
<221> NAME/KEY: MOD_RES
<222> LOCATION: (44)..(45)
<223> OTHER INFORMATION: May or may not be present
<220> FEATURE:
<223> OTHER INFORMATION: see specification as filed for detailed
      description of substitutions and preferred embodiments

<400> SEQUENCE: 13

Ile Pro Ser Ser Pro Val His Leu Lys Arg Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Gly Ala Leu Leu Xaa Gly Leu
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(18)
<223> OTHER INFORMATION: Ile, Leu or nor-leucine and this region may
      encompass 1 to 8 residues
<220> FEATURE:
<221> NAME/KEY: MOD_RES
<222> LOCATION: (19)..(19)
<223> OTHER INFORMATION: Lys, Arg, His, Trp, Phe, Tyr or Ornithine
<220> FEATURE:
<221> NAME/KEY: MOD_RES
<222> LOCATION: (20)..(38)
<223> OTHER INFORMATION: Ile, Leu or nor-leucine and this region may
      encompass 1 to 19 residues
<220> FEATURE:
<221> NAME/KEY: MOD_RES
<222> LOCATION: (43)..(43)
<223> OTHER INFORMATION: Met, Met oxidized on the sulfur atom, Ile, Leu,
      nor-leucine and may or may not be present
<220> FEATURE:
<221> NAME/KEY: MOD_RES
<222> LOCATION: (44)..(45)
<223> OTHER INFORMATION: May or may not be present
<220> FEATURE:
<223> OTHER INFORMATION: see specification as filed for detailed
      description of substitutions and preferred embodiments

<400> SEQUENCE: 14

Ile Pro Ser Ser Pro Val His Leu Lys Arg Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Gly Ala Leu Leu Xaa Gly Leu
        35                  40                  45

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (31)..(31)
<223> OTHER INFORMATION: Met, Met oxidized on the sulfur atom, Ile, Leu,
      nor-leucine and may or may not be present
<220> FEATURE:
<221> NAME/KEY: MOD_RES
<222> LOCATION: (32)..(33)
<223> OTHER INFORMATION: May or may not be present
<220> FEATURE:
<223> OTHER INFORMATION: see specification as filed for detailed
      description of substitutions and preferred embodiments

<400> SEQUENCE: 15

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
            20                  25                  30

Leu

<210> SEQ ID NO 16
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(5)
<223> OTHER INFORMATION: May or may not be present
<220> FEATURE:
<221> NAME/KEY: MOD_RES
<222> LOCATION: (13)..(20)
<223> OTHER INFORMATION: Ile, Leu or nor-leucine and this region may
      encompass 1 to 8 residues
<220> FEATURE:
<221> NAME/KEY: MOD_RES
<222> LOCATION: (21)..(21)
<223> OTHER INFORMATION: Lys, Trp, Phe, Tyr or Ornithine
<220> FEATURE:
<221> NAME/KEY: MOD_RES
<222> LOCATION: (22)..(40)
<223> OTHER INFORMATION: Ile, Leu or nor-leucine and this region may
      encompass 1 to 19 residues
<220> FEATURE:
<221> NAME/KEY: MOD_RES
<222> LOCATION: (41)..(41)
<223> OTHER INFORMATION: Lys, Trp, Phe, Tyr or Ornithine
<220> FEATURE:
<221> NAME/KEY: MOD_RES
<222> LOCATION: (42)..(49)
<223> OTHER INFORMATION: Ile, Leu or nor-leucine and this region may
      encompass 3 to 8 residues
<220> FEATURE:
<221> NAME/KEY: MOD_RES
<222> LOCATION: (50)..(50)
<223> OTHER INFORMATION: Lys, Trp, Phe, Tyr or Ornithine
<220> FEATURE:
<221> NAME/KEY: MOD_RES
<222> LOCATION: (51)..(58)
<223> OTHER INFORMATION: Ile, Leu or nor-leucine and this region may
      encompass 3 to 8 residues
<220> FEATURE:
<221> NAME/KEY: MOD_RES
<222> LOCATION: (59)..(59)
<223> OTHER INFORMATION: Lys, Trp, Phe, Tyr or Ornithine
<220> FEATURE:
<221> NAME/KEY: MOD_RES
<222> LOCATION: (60)..(67)
<223> OTHER INFORMATION: Ile, Leu or nor-leucine and this region may
      encompass 3 to 8 residues
```

```
<220> FEATURE:
<221> NAME/KEY: misc_feature
<222> LOCATION: (41)..(67)
<223> OTHER INFORMATION: This region may encompass 0 to 3 4-9 residue
      repeating units
<220> FEATURE:
<221> NAME/KEY: MOD_RES
<222> LOCATION: (72)..(72)
<223> OTHER INFORMATION: Met, Met oxidized on the sulfur atom, Ile, Leu
      or nor-leucine and may or may not be present
<220> FEATURE:
<221> NAME/KEY: MOD_RES
<222> LOCATION: (73)..(74)
<223> OTHER INFORMATION: May or may not be present
<220> FEATURE:
<223> OTHER INFORMATION: see specification as filed for detailed
      description of substitutions and preferred embodiments

<400> SEQUENCE: 16

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Gly Ala Leu Leu Xaa Gly Leu
65                  70

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Phe Gly Ile Pro Cys Cys Pro Val His Leu Lys Arg Leu Leu Ile Val
1               5                   10                  15

Val Val Val Val Val Leu Ile Val Val Val Ile Val Gly Ala Leu Leu
            20                  25                  30

Met Gly Leu
        35

<210> SEQ ID NO 18
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45
```

```
Leu Ala Glu Arg Tyr Ser Val Ile Leu Leu Asp Thr Leu Leu Gly Arg
 50                  55                  60

Met Leu Pro Gln Leu Val Cys Arg Leu Val Leu Arg Cys Ser Met
 65                  70                  75
```